(12) United States Patent
Högerle et al.

(10) Patent No.: US 10,702,284 B2
(45) Date of Patent: Jul. 7, 2020

(54) TOOL FITTING ATTACHMENT FOR A SURGICAL DRILL WITH ADDITIONAL MANUAL DRIVE UNIT, AND SURGICAL DRILL

(71) Applicant: Aesculap AG, Tuttlingen (DE)

(72) Inventors: Roland-Alois Högerle, Tuttlingen (DE); Jan Steinhauser, Sigmaringen (DE)

(73) Assignee: AESCULAP AG, Tuttlingen (DE)

( * ) Notice: Subject to any disclaimer, the term of this patent is extended or adjusted under 35 U.S.C. 154(b) by 185 days.

(21) Appl. No.: 15/744,960

(22) PCT Filed: Jul. 6, 2016

(86) PCT No.: PCT/EP2016/065988
§ 371 (c)(1),
(2) Date: Jan. 15, 2018

(87) PCT Pub. No.: WO2017/012877
PCT Pub. Date: Jan. 26, 2017

(65) Prior Publication Data
US 2018/0206856 A1 Jul. 26, 2018

(30) Foreign Application Priority Data

Jul. 22, 2015 (DE) .......................... 10 2015 111 877
Jul. 22, 2015 (DE) .......................... 10 2015 111 878

(51) Int. Cl.
*A61B 17/16* (2006.01)
*B25B 23/14* (2006.01)

(52) U.S. Cl.
CPC .......... *A61B 17/1624* (2013.01); *A61B 17/16* (2013.01); *A61B 17/162* (2013.01);
(Continued)

(58) Field of Classification Search
CPC . A61B 17/19; A61B 17/1615; A61B 17/1617; A61B 17/162; A61B 17/1622;
(Continued)

(56) References Cited

U.S. PATENT DOCUMENTS 3,120,845 A 2/1964 Horner
4,487,270 A * 12/1984 Huber .................... B23B 45/02
173/176

(Continued)

FOREIGN PATENT DOCUMENTS

CN 101547771 A 9/2009
CN 103596730 A 2/2014
(Continued)

OTHER PUBLICATIONS

German Search Report for German Application No. 10 2015 111 878.5, with English translation, dated May 9, 2016, 11 pages.
(Continued)

*Primary Examiner* — Eric S Gibson

(57) ABSTRACT

A tool fitting attachment for a surgical drill can include a drive-side coupling for mounting on a drive unit which provides a torque via a motor, and an output-side coupling for receiving a tool. A drive unit is integrated between the two couplings and can be manually operated. A surgical drill can include an electric motor which is connected via the drive-side coupling of the tool fitting attachment.

15 Claims, 3 Drawing Sheets

Figure 1:
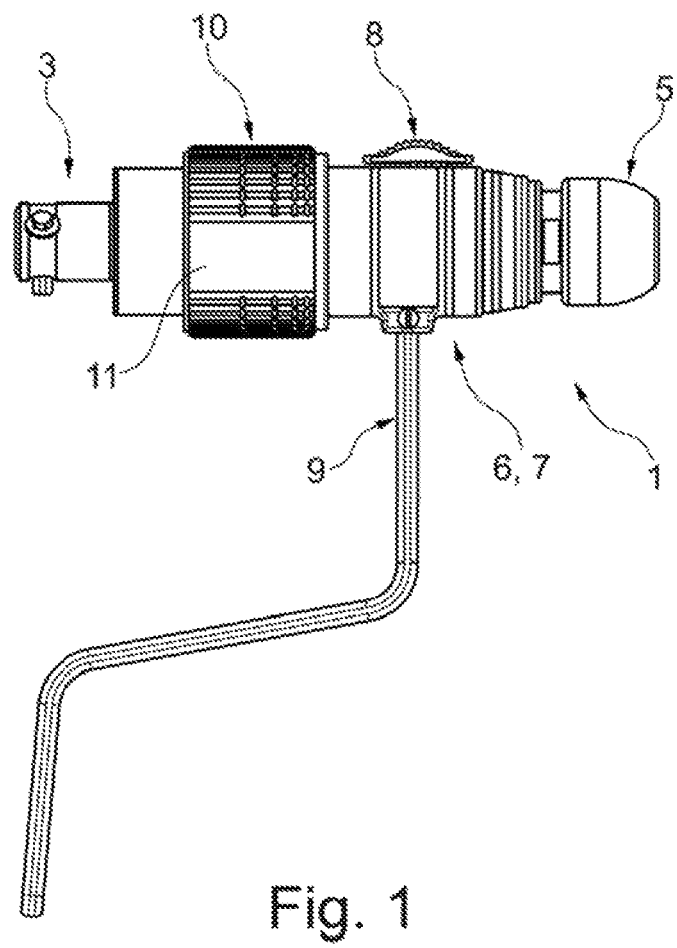

(52) U.S. Cl.
CPC ...... *A61B 17/1617* (2013.01); *A61B 17/1626* (2013.01); *B25B 23/141* (2013.01); *A61B 17/1622* (2013.01)

(58) Field of Classification Search
CPC . A61B 17/1624; A61B 17/1628; B25B 23/14; B25B 23/1405; B25B 23/141; B25B 23/147; B25B 23/1475
See application file for complete search history.

(56) References Cited

U.S. PATENT DOCUMENTS

| | | | |
|---|---|---|---|
| 5,458,206 A * | 10/1995 | Bourner | B25B 23/14 173/104 |
| 5,613,585 A | 3/1997 | Tiede | |
| 5,619,891 A | 4/1997 | Tiede | |
| 5,741,263 A | 4/1998 | Umber et al. | |
| 5,794,715 A * | 8/1998 | Norman | A61B 17/162 173/104 |
| 5,885,200 A | 3/1999 | Walen | |
| RE37,905 E * | 11/2002 | Bourner | B25B 23/14 173/178 |
| 6,817,458 B1 | 11/2004 | Gauthier | |
| 7,181,997 B1 | 2/2007 | Rinner et al. | |
| 7,926,390 B2 | 4/2011 | Bennett | |
| 8,597,316 B2 | 12/2013 | McCombs | |
| 8,786,233 B2 | 7/2014 | Fair et al. | |
| 8,801,713 B2 | 8/2014 | del Rio et al. | |
| 8,985,593 B1 * | 3/2015 | Gao | A61B 17/162 279/74 |
| 9,113,917 B2 | 8/2015 | del Rio et al. | |
| 9,381,023 B2 | 7/2016 | del Rio et al. | |
| 9,681,879 B2 | 6/2017 | del Rio et al. | |
| 9,937,009 B2 * | 4/2018 | Schroeder | A61B 17/1622 |
| 2002/0058958 A1 * | 5/2002 | Walen | A61B 17/1615 606/170 |
| 2002/0151902 A1 * | 10/2002 | Riedel | A61B 17/162 606/80 |
| 2003/0110901 A1 | 6/2003 | Shiao | |
| 2006/0048610 A1 | 3/2006 | Hu | |
| 2006/0053974 A1 | 3/2006 | Blust et al. | |
| 2006/0248987 A1 * | 11/2006 | White | A61B 17/1624 81/62 |
| 2007/0260257 A1 * | 11/2007 | Phan | A61B 17/1617 606/84 |
| 2009/0234365 A1 * | 9/2009 | Gross | A61B 17/8875 606/104 |
| 2010/0063524 A1 | 3/2010 | McCombs | |
| 2010/0163264 A1 | 7/2010 | Simm et al. | |
| 2011/0061500 A1 * | 3/2011 | Huang | B25B 23/1427 81/474 |
| 2012/0055296 A1 * | 3/2012 | Landowski | B25B 23/1427 81/474 |
| 2014/0102741 A1 * | 4/2014 | Sekino | B25B 21/02 173/181 |
| 2014/0277203 A1 * | 9/2014 | Atoulikian | A61B 17/7091 606/86 A |
| 2014/0327382 A1 | 11/2014 | Fair et al. | |
| 2015/0021062 A1 * | 1/2015 | Sekino | B25B 21/007 173/183 |
| 2015/0148176 A1 * | 5/2015 | Schroeder | A61B 17/1622 475/269 |
| 2015/0351777 A1 * | 12/2015 | Lizardi | A61B 17/1622 606/80 |
| 2015/0367487 A1 * | 12/2015 | Nino | A61B 17/8875 81/473 |
| 2016/0089154 A1 * | 3/2016 | Chien | A61B 17/1626 606/79 |
| 2016/0325414 A1 * | 11/2016 | Mizuno | B25B 21/02 |
| 2017/0156813 A1 * | 6/2017 | Cutler | A61B 90/03 |
| 2017/0314711 A1 * | 11/2017 | Helstern | F16L 19/00 |
| 2017/0367748 A1 * | 12/2017 | Plotkin | B25G 1/105 |
| 2018/0104801 A1 * | 4/2018 | Bakula | B25B 15/02 |
| 2018/0206853 A1 * | 7/2018 | Steinhauser | A61B 17/84 |
| 2018/0206856 A1 * | 7/2018 | Hogerle | B25F 3/00 |
| 2018/0242982 A1 | 8/2018 | Laughlin et al. | |
| 2019/0059910 A1 * | 2/2019 | Adams | A61B 17/1675 |
| 2019/0125421 A1 * | 5/2019 | Smith | A61B 17/8875 |
| 2019/0231447 A1 | 8/2019 | Ebbitt et al. | |

FOREIGN PATENT DOCUMENTS

| | | |
|---|---|---|
| DE | 1871193 U | 4/1963 |
| DE | 1214826 B | 4/1966 |
| DE | 4342464 A1 | 6/1995 |
| DE | 19730300 A1 | 9/1998 |
| DE | 29723472 U1 | 9/1998 |
| DE | 19951888 A1 | 5/2000 |
| DE | 19942292 A1 | 10/2000 |
| DE | 102005034114 A1 | 2/2006 |
| DE | 102006057283 A1 | 6/2008 |
| DE | 102007048928 A1 | 4/2009 |
| DE | 102011088252 A1 | 6/2013 |
| EP | 1080848 A2 | 3/2001 |
| EP | 2701879 A1 | 3/2014 |
| WO | 2013020877 A1 | 2/2013 |

OTHER PUBLICATIONS

German Search Report for German Application No. 10 2015 111 877.7, with English translation, dated May 11, 2016, 14 pages.

International Search Report and Written Opinion for International Application No. PCT/EP2016/065988, dated Mar. 21, 2017, 18 pages.

Non Final Office Action for U.S. Appl. No. 15/744,957, dated Aug. 23, 2019, 20 pages.

German Search Report for German Application No. 10 2015 111 878.5, with translation, dated May 9, 2016, 11 Pages.

International Search Report and Written Opinion for International Application No, PCT/EP2016/065986, dated Mar. 21, 2017, 12 Pages.

Notice of Allowance for U.S. Appl. No. 15/744,957, dated Nov. 21, 2019, 7 pages.

Chinese Office Action Application No. 201680043019.1 dated Mar. 24, 2020, 21 pages.

* cited by examiner

TOOL FITTING ATTACHMENT FOR A SURGICAL DRILL WITH ADDITIONAL MANUAL DRIVE UNIT, AND SURGICAL DRILL

RELATED APPLICATIONS

This application is the United States national phase entry of International Application No. PCT/EP2016/065988, filed Jul. 6, 2016, which is related to and claims the benefit of priority of German Application No. 10 2015 111 877.7, filed Jul. 22, 2015 and German Application No. 10 2015 111 878.5, filed Jul. 22, 2015. The contents of International Application No. PCT/EP2016/065988, German Application No. 10 2015 111 877.7, and German Application No. 10 2015 111 878.5, filed Jul. 22, 2015 are incorporated by reference herein in their entireties.

FIELD

The invention relates to a tool fitting attachment for a medical motor-driven machine tool such as a surgical drill which may also be referred to or used as a surgical screwdriver, comprising a drive-side coupling for mounting on a drive unit/motor which provides a torque by means of an (electric) motor, such as a drive motor comprising an electric motor and an output-side coupling/tool fitting chuck for receiving a tool such as a screwdriver, a drill or similar turning tools.

BACKGROUND

In medical engineering, especially in surgery, in particular surgical interventions bone screws are set, for example so-called pedicle screws which are used in spinal surgery. For this purpose, at first a drilling operation has to be carried out so that then a screw can be set into each hole drilled into the vertebra body. Unfortunately, all bones/vertebrae to be treated have a different brittleness. Therefore, a certain sensitiveness is required to accurately set the bore and to introduce the screw in a non-destructive manner/i.e. without damaging the vertebra body. However, especially critical are the last phase of the drilling operation and the last phase of the screwing operation. Until then, a lot of rotational movements are required to create the borehole and to introduce the screw sufficiently deeply so that the risk of tear-out of the vertebra bone or over-tightening of the screw will increase especially in the respective final phase of the drilling and screwing operation.

Manual screwing-in of surgical screws results in rapid fatigue of the surgeon's hand and arm muscles due to the repetitive movement, however. This may result in a negative operation outcome and also may cause long-term symptoms among physicians.

Therefore, it has always been desirable to make use of a motor drive unit (electric, hydraulic or pneumatic motor) so as to provide a torque. In so doing, frequently electric motor drive units, i.e. drive motors comprising an electric motor, are used which are either supplied with power depending on a battery/an accumulator or else make use of an external power supply via a cable.

There are known already so-called transfixion wire chucks constituting attachments for surgical drills which make use of a lever for fulfilling a specific function. A transfixion wire is guided through the machine. When the lever is pulled, the wire is clamped in the motor so that it can be made to rotate by the drive unit. In this way, the wire can be turned into a tissue. Upon release of the lever, the wire can be moved in an axially and rotationally free manner in the motor. This principle is further pursued also in other medical devices.

From the state of the art, for example an electric cable-bound screwing pistol is known from U.S. Pat. No. 8,786,233 B2, which belongs to the same family as EP 2 701 879 A1. There an electric ratchet for a driven screwdriver is disclosed. Said known ratchet is designed so that, unless a trigger is actuated, the electronic ratchet is activated. The user may choose at an additional operating unit between clockwise and anti-clockwise rotation as well as blocking into both directions.

The ratchet is electrically configured/activatable resulting in the fact that for ensuring the ratchet to block such high current flows in the motor that a strong heat development will occur. In addition, acoustic feedback is missing. In this case, manual ratcheting carried out for drilling in the final drilling phase, for example, or mechanical ratcheting used during thread-cutting, as it is also used in the last phase of screwing, for example, is not provided. As the system is cable-bound, also the reach/freedom of movement is strongly limited. Furthermore, it is a drawback of this system that a closed system is presented and inadvertent actuation of the trigger during manual screwing results in a sudden penetration of the screw or in a sudden continued drilling. This is disastrous when applied to a patient, however.

Screw attachments are also known from other manufacturers, for example the Surgical Drill Set 510.01 manufactured by Synthesis. An attachment which reduces the output speed of the drill pistol to about 300 Rpm can be attached to said drill pistol. For use, it is additionally prescribed to attach a torque limiter to this screw attachment. It is a drawback that such torque limiters are not adjustable and are easily available only at predefined values of 0.4 Nm, 0.8 Nm, 1.5 Nm and 4 Nm. Furthermore, this system cannot be used for manual screwing and tightening of screws. Therefore, a tool change is always required. In practice, also the torque limitation turns out to lack flexibility. Manual screwing-in of a screw by a mechanical ratchet, for example by means of a screwdriver having an integrated ratchet, is not useful, either, although it is advantageous in this case that changing the grip during the screwing operation is avoided. It is a drawback that, despite the use of a ratchet, such repetitive movement resulting in fatigue of the muscles is still required and thus may also directly negatively affect the outcome of operation. The symptoms of the physicians are not avoided, either.

It is another drawback of the various systems that they can be employed either for plate screw joints only or for polyaxial screws only. Polyaxial screws in this context are e.g. screws having a spherical screw head which is enclosed by a case so that the case is freely adjustable relative to the longitudinal axis of the screw. In particular pedicle screws are configured in this way.

SUMMARY

Therefore, it is the object of the present invention to provide a tool fitting attachment usable both for pedicle screws/polyaxial screws and for plate screw joints which eliminates or at least alleviates the afore-described drawbacks. Especially, it is also intended to reduce the physical load of the user (surgeon) when introducing screws. Furthermore, the invention is especially intended to enable the user (surgeon) to obtain safe machine screwing. In addition, the adjustment of the motor speed is intended to be selectable so that the user can precisely adjust the desired speed.

Between the two couplings for connecting a motor to the one input coupling and for fitting/connecting a tool to the outer output coupling a drive unit which is manually operable/operated by manual force in the form of a ratchet is included which by means of the ratchet handle/manual operating unit of the ratchet itself can be brought into a first operating position at which the torque is transmitted from the input coupling to the output coupling, while bypassing the ratchet function, and can be brought into a second operating position at which the two couplings are separated by the torques and instead a manual torque introduced via the ratchet function by the ratchet handle/manual operating unit is transmitted to the output coupling.

Instead of a motor-driven torque transmission, then a more precisely adjustable manual torque transmission can be effectuated. This is possible without having to carry out a tool change and without having to operate the machine itself in any way separately from the ratchet. That is, the aforementioned operating positions are adjustable exclusively by functions and means internal to the ratchet (ratchet handle) and not by functions of the ratchet and the unit communicating with each other. This ensures that the two aforementioned operating positions can be adjusted as well as maintained irrespective of the way in which the machine is operated, for example by operating the motor, pressing the tool onto the bone to be drilled/the screw to be screwed in via the machine/the grip of the machine etc. Thus, safe operation is possible. Damage to the patient or to the physician is prevented. Precise use is enabled.

It may be provided by constructional design to configure the ratchet to include two torque transmission elements (sleeves) which bear respective tooth systems acting in opposite directions and can be alternately switched to operate depending on the manual selection so as to transmit a torque acting clockwise or anti-clockwise from a manual input component such as a ratchet casing to a ratchet output element such as an output sleeve. Between the ratchet output element and the two torque transmission elements a type of selecting component such as a selecting plate/sleeve is arranged which can be manually adjusted so as to enter into operative engagement with either of the torque transmission elements. Moreover, the selecting component may be adjusted via the ratchet output element upon actuation thereof by means of the ratchet handle to adopt an out-of-function position of the ratchet at which the ratchet is no longer capable of transmitting a manually introduced torque to the ratchet output element, but at the same time the ratchet output element at this operating position directly connects the two couplings via the torque.

For example, the ratchet output element constitutes a sleeve which encompasses an output shaft of the tool fitting in an axially movable but rotationally fixed manner and has a gearing such as a spur gearing which, as a function of the axial position of the ratchet output element relative to the output shaft of the tool fitting, can be engaged in a direct/indirect output element of the input coupling. Furthermore, the ratchet output element includes a type of driver such as a driving pin or projection acting upon the afore-mentioned selecting component of the ratchet and driving the latter, during adjustment of the ratchet output element into the out-of-operation position of the ratchet, to a position at which operative engagement between the selecting component and the two torque transmission elements of the ratchet is excluded. In that case, a torque transmission from the motor to the output coupling is enabled, although the ratchet function is put out of operation. When, however, the ratchet output element is adjusted to a position at which there is no direct operative engagement with the direct/indirect output element of the input coupling, the selecting component is, e.g. resiliently, urged into a position at which it can be operatively engaged selectively in either of the two torque transmission elements. In that case, a torque transmission from the motor to the output coupling is interrupted, although the ratchet function is put into operation.

In order to facilitate handling of the ratchet, the handle may be e.g. a lever supported on the casing of the ratchet so as to rotate the latter around the output shaft of the tool fitting and, in this way, introduce a manual torque to the ratchet. Simultaneously, the lever may be pivoted in the longitudinal direction of the output shaft of the tool fitting on the ratchet casing and may act at its end protruding into the interior of the ratchet upon the ratchet output element so as to axially move the latter and thus to set the two aforementioned positions for putting the ratchet function out of/into operation.

In this case, only the one handle inherent to the ratchet has to be operated so as to set the two positions and also to introduce manual torque to the ratchet.

It is of advantage when the drive unit (casing) arranged for providing the torque by manual force is connected to a ratchet unit/ratchet device or a pawl (inside the casing) or is integrated with the latter. A rotating movement within a limited working compartment, e.g. for loosening or tightening screwed connections, then is efficiently enabled. For this, a gearing may be used inside the ratchet unit/ratchet device or pawl, for example requiring an angle of rotation of at least 10° to 15°, so as to obtain a rotation of the output element. However, it is also possible to use fine tooth ratchets so that an angle of rotation of about 5° is sufficient already to produce a movement of the screw.

It is further advantageous when the ratchet or pawl is connected downstream of the manual drive unit (ratchet input element/ratchet casing), i.e. is inserted between the manual drive unit and the output-side coupling (output coupling). In this way, efficient operation may be achieved.

In order to facilitate acoustic feedback, it is of advantage when the ratchet unit/ratchet device is a mechanical ratchet. In addition, it is possible to switch between clockwise rotation and anti-clockwise rotation via a direction selection control unit. In this manner, switching positions for screwing in or instead for screwing out may be provided.

In order to avoid faulty operation, it is of advantage when the direction selection control unit is integrated so that actuation is possible only during electrical operation.

Furthermore, it is advantageous when the manual drive unit is connected to the lever adapted to be gripped by hand. The lever may take a Z, N or S shape.

When a torque limiter is incorporated, drilling or screwing beyond a limit torque can be prevented. Thus, the operating safety is increased.

An advantageous embodiment is also characterized in that the torque limiter is arranged between the drive-side coupling and the ratchet device/ratchet unit.

It is useful when the manual drive unit is connected to a disconnect coupling so that in the case of actuation of the manual drive unit a motor-driven torque transmission to the output-side coupling is excluded. Advantageously, the disconnect coupling is adapted to be actuated at any time. This enables a smooth or digital change between the electrical and manual operating modes.

It is of advantage when the disconnect coupling is connected to the lever of the manual drive unit so that, upon properly actuating the lever of the ratchet, the disconnect coupling is actuated.

The invention further relates to a surgical drill and, resp., a surgical screwdriver comprising an electric motor that is connected via the drive-side coupling of the tool fitting attachment according to the invention for introducing a torque to said attachment.

In other words, the invention thus relates to a tool fitting attachment which allows the user to decide at any time by a manual operating mode to manually screw in the screw without changing the tool. This will give the user more direct feedback on the state of the bone. A mechanical ratchet including switchable anti-clockwise and clockwise rotation renders such manual screwing more convenient. In order to prevent inadvertent change-over during screwing-in, the direction of rotation (anti-clockwise/clockwise rotation) can be changed in the electric mode only.

A freely adjustable torque limitation which is effective in the electric mode only assists the user in selecting the correct point in time from which he/she intends to start manual screwing. It may be additionally used as a safety function. The free adjustability allows for flexible adaptation to various applications. A locking mechanism prevents inadvertent adjusting.

A mechanical realization of a manual drive on a surgical drill is facilitated. More exactly, a realization of a manual drive is obtained in an attachment for a surgical drill. Additionally, a ratchet function is integrated. Change of the direction of rotation of the ratchet function is provided. A lever enables a smooth or digital change between an electrical operating mode and a manual operating mode. The additional combination with a freely adjustable torque limitation which may engage or may be infinitely variable but may also dispense with a Nm scale is of advantage. This function can be realized in one single attachment.

Electric and manual screwing is enabled without any tool change. The physical load of the surgeon is reduced. The operating safety is increased as actuating a "trigger" is uncritical in the manual mode. The ratchet in the manual mode ensures increased convenience during manual screwing. Acoustic feedback is facilitated by the ratchet causing a ratchet sound. The safety is increased by an adjustable torque limitation. Equally, acoustic feedback is enforced when the torque limitation slips. By means of a matching coupling the tool fitting attachment can be used with each motor in a purely mechanical manner. No electronics which might cause problems concerning sterilizing capability are required. As a result, simple operation is obtained.

Manual screwing of screws requires great expenditure of time and force. At the same time physicians cannot screw merely by machine as the tactile feedback is missing. The invention allows to screw in screws optionally by hand or by machine without any tool change. In support thereof, additionally a limiting torque can be freely adjusted.

The attachment is coupled to the motor via the "plug-and-play" coupling. At the distal end another "plug-and-play" coupling is provided which is capable of accommodating a screwing tool. The disengaging torque can be set by unlocking and adjusting the rotary handle at an electric drive. After setting the torque, the rotary handle can be locked. The rotary handle may include a grid so as to assist the user during application.

By pulling the lever in the longitudinal direction of the tool fitting shaft, as afore-indicated already, the user may manually screw screws into the bone via the ratchet. In the implemented example, the output is completely disconnected from the electric drive (motor), which additionally increases the operating safety. Upon release of the lever the connection to the electric drive is restored. The manual drive is implemented in the form of an adjustable ratchet. By another operating element, the user can change between anti-clockwise rotation and clockwise rotation. In order to prevent inadvertent adjustment, operation is possible in the electrical operating mode only. When designing the operating element, importance is attached to an intuitive operation. As a consequence, in the implemented example the front position of the operating element corresponds to the clockwise rotation relative to the penetration of a screw.

BRIEF DESCRIPTION OF THE DRAWING FIGURES

Figure 2:
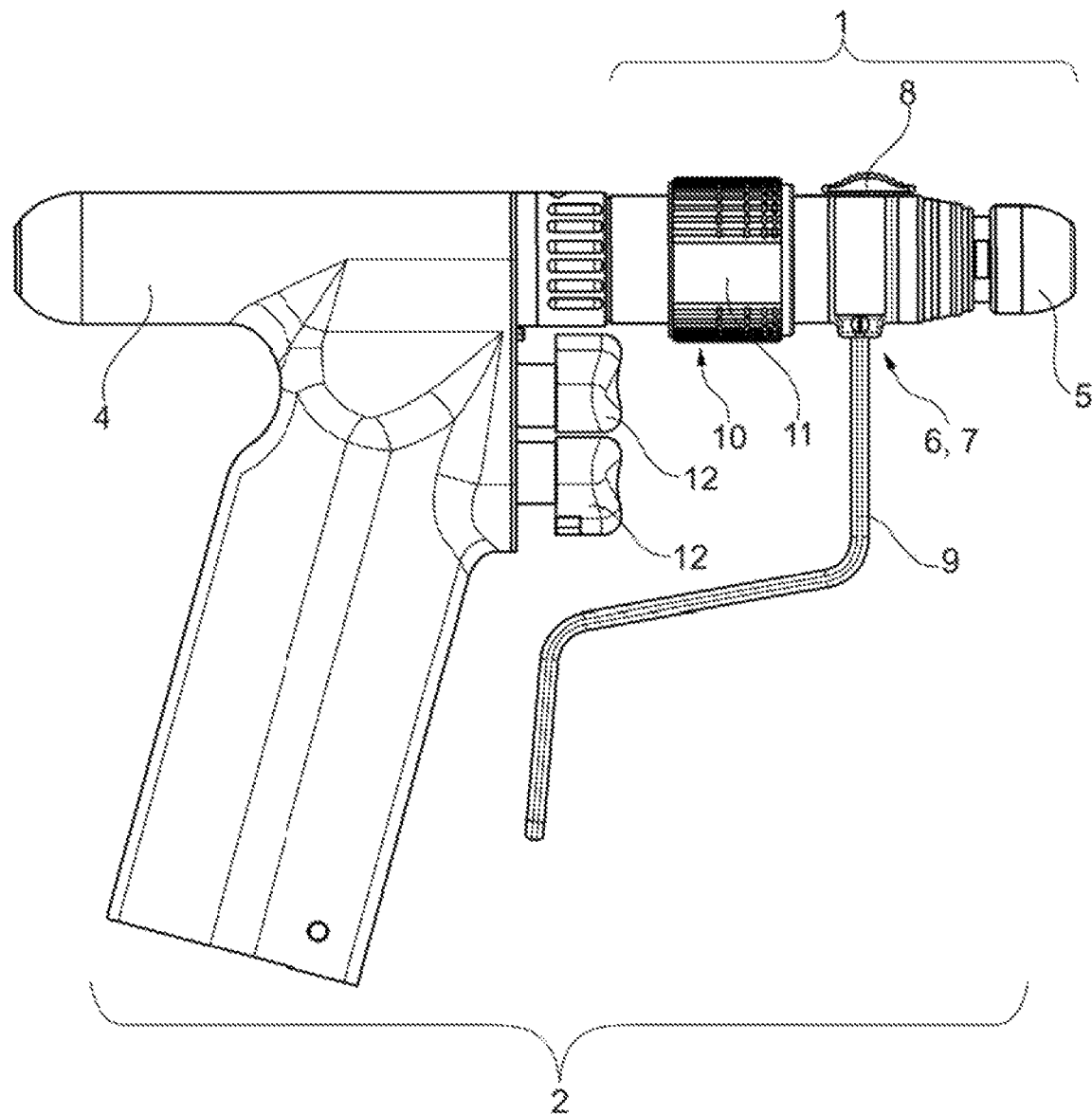
Figure 3:
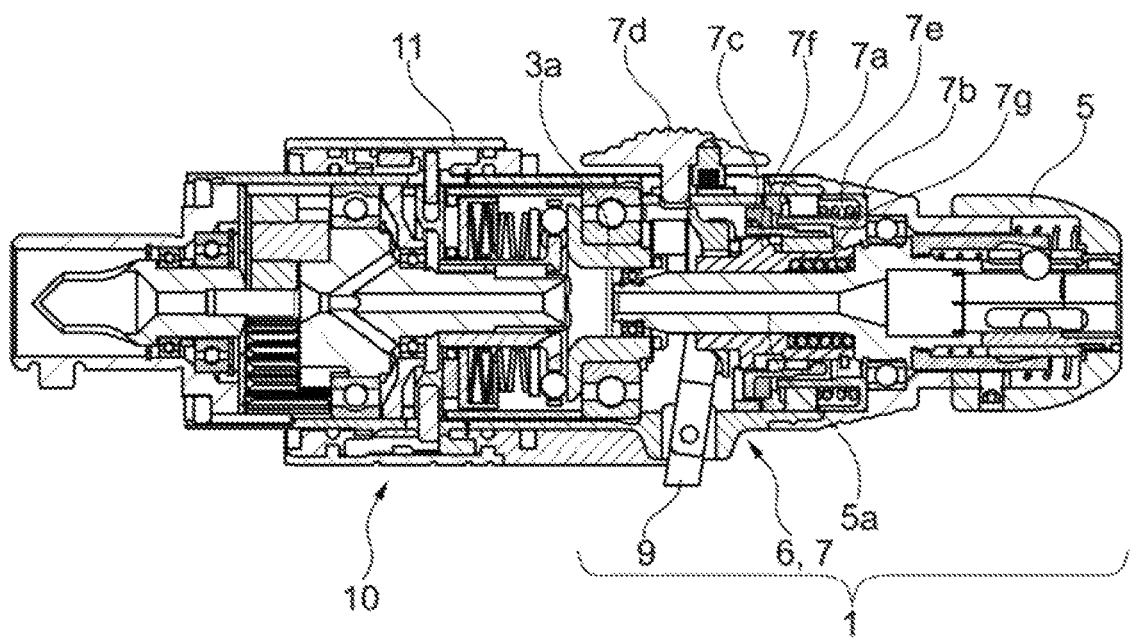

The foregoing summary and the following description will be better understood in conjunction with the following non-limiting illustrations showing a first embodiment, wherein:

FIG. 1 shows a side view of a tool fitting attachment according to the invention, FIG. 2 shows a surgical drill according to the invention which may as well be used as a surgical screwdriver comprising a tool fitting attachment adapted according to the invention in a side view, and FIG. 3 shows a longitudinal sectional view across a drill according to the invention.

The Figures only serve for the comprehension of the invention. Identical elements are provided with like reference numerals.

DETAILED DESCRIPTION

In FIG. 1 a tool fitting attachment 1 according to the invention is shown. It is provided for the surgical drill 2 shown in FIG. 2 and is coupled thereto.

Referring to FIG. 1, it is explained that the tool fitting attachment 1 includes a drive-side coupling (input coupling) 3 for mounting a drive unit 4 (see FIG. 2) such as a motor, motor-gear-unit etc. The drive-side coupling 3 is configured as a "plug-and-play" coupling. Thus it is a coupling without reconfiguration or a coupling that is free from user-dependent readjustment. The drive unit may be a medical/surgical machine such as a drilling/screwing/milling machine, as it is sufficiently known from the state of the art and therefore need not be described in detail here.

While at the proximal end of the tool fitting attachment 1 the drive-side coupling 3 is present, at the distal end an output-side coupling (output coupling) 5 is present.

Between the two couplings 3 and 5, with the output-side coupling 5 also being designed as a "plug-and-play" coupling, a separate drive unit 6 that is manually operable, i.e. operable by manual force, is provided. The drive unit 6 is connected to/integrated in a ratchet device/ratchet unit 7, with the ratchet device/ratchet unit 7 being in the form of a manual ratchet.

Concretely speaking, the ratchet 7 according to FIG. 3 consists of a casing as the manual drive unit 6 in which two sleeve-shaped torque transmission elements are accommodated to rotationally fixed with the casing 6, at least one torque transmission element of which is held to be axially movable relative to the other torque transmission element. Both torque transmission elements preferably include at their one front end a respective gearing so as to be brought, alternately and selectively depending on their axial position relative to each other, in mesh with an intermediate/selection component in the form of a disk or a ring being axially adjacent to the torque transmission elements.

Said relative axial position can be adjusted by means of a manually operable slide. The slide is coupled to either of the two torque transmission elements so as to axially displace the same. This causes the at least one axially movable torque transmission element to be brought in or out of mesh with the intermediate/selection component. The intermediate/selection component is equally held to be axially movable and is biased by means of a spring in the direction of the two intermediate/selection components. When thus the one torque transmission element is axially forced into mesh by means of the slide against the intermediate/selection component, the latter is axially displaced against the spring bias, which causes the mesh with the other torque transmission element to be disengaged and vice versa.

The gearings of the two torque transmission elements act in opposite directions in such manner that they may transmit a clockwise or anti-clockwise torque and cause freewheeling in the respective other direction. Depending on the selected torque transmission element, in this way a clockwise or anti-clockwise torque may be transmitted starting from the manual drive unit 6 via the ratchet. Further, the intermediate/selection component is supported to be axially movable but rotationally fixed on a sleeve-shaped ratchet output element which, in turn, is supported to be rotationally fixed but axially movable on a shaft of the output-side coupling 5.

The ratchet output element preferably includes on its front end a gearing via which the ratchet output element may enter into torque-transmitting mesh with an output element of the input-side coupling 3 in response to its axial position relative to the shaft of the output-side coupling 5 so as to transmit a torque from the motor to the output-side coupling 5.

The manual drive unit (casing) 6 is activated and driven via a lever 9. To that end, the lever 9 is configured in the type of a crank and is adapted to the size of a human hand. I.e. the lever 9 is supported in the casing 6 so that the casing 6 can be rotated via said lever about the central axis of the tool fitting and in this way the torque transmission elements can be driven. The lever 9 is pivoted in the axial direction of the tool fitting, however, as is shown in FIG. 3. A lever extension protruding into the casing interior is coupled to the ratchet output element so that the latter may be displaced in the axial direction by pivoting the lever 9.

The ratchet output element includes a driver in the form of a radial projection which directly or indirectly acts upon the intermediate/selection component of the ratchet so as to drive the same, where appropriate, corresponding to the axial movement of the ratchet output element.

When thus the ratchet output element is axially displaced via the lever 9 against the output element of the input-side coupling 3 to enter into torque-transmitting mesh, the intermediate/selection component of the ratchet is driven into an axial position at which it cannot enter into mesh with either of the two torque transmission elements any more. Although in this case a torque is transmitted from the motor to the output-side coupling 5, the ratchet function is put out of operation, however. When, however, the ratchet output element is axially displaced away from the output element of the input-side coupling 3 via the lever 9 (no more mesh), the intermediate/selection component of the ratchet is driven into an axial position at which it may mesh with either of the two torque transmission elements. Although in that case no torque can be transmitted from the motor to the output-side coupling 5, the ratchet function is put into operation, however. In this way, quasi a disconnect coupling is realized.

In this manner, two functions are imparted to the lever 9, namely:
putting the ratchet function into/out of operation while simultaneously connecting/disconnecting the motor to/from the output-side coupling 5 and
manually operating the ratchet, Between the manual ratchet, especially between the ratchet output element and the drive-side coupling 3, a torque limiter 10 is further provided. It can be manually adjusted, unlocked and locked, for example via a rotary handle. The rotary handle is provided with the reference numeral 11.

FIGS. 2 and 3 illustrate the complete setup of the surgical drill 2 including the inserted tool fitting attachment 1. Two actuating buttons 12 are used by which different functions of the drill 2 can be controlled/set.

The invention claimed is:

1. A tool fitting attachment for a surgical machine, comprising:
    a drive-side coupling for mounting to a drive unit which provides a torque by a motor; and
    an output-side coupling for receiving a tool,
    wherein, between the two couplings, a manually operated drive unit is integrated,
    wherein the drive-side coupling is configured for coupling the tool fitting attachment to the drive unit via a torque, and
    wherein the output-side coupling is configured for receiving or connecting the medical tool by transmitting a torque,
    the tool fitting attachment further comprising a manually operable ratchet unit having an effective direction of rotation that can be manually changed, the ratchet unit being arranged between the drive-side coupling and the output-side coupling and having a torque introducing member/ratchet input component manually torque-operated via a handle and configured as a casing and a guide shaft/ratchet output component which is in torque engagement with the output-side coupling so as to transmit, in response to the effective direction of rotation, a manually introduced torque to the output-side coupling, the guide shaft/ratchet output component being operable as a disconnect coupling and axially movable relative to the output-side coupling by the handle in such manner that, at a first movement position, the handle connects the drive-side coupling to the output-side coupling via the torque while bypassing the ratchet unit and puts the ratchet unit out of operation and, at a second movement position, disconnects a torque connection between the drive-side coupling and the output-side coupling and puts the ratchet unit into operation.

2. The tool fitting attachment according to claim 1, wherein the torque introducing member/ratchet input component and the guide shaft/ratchet output component can be coupled via the torque through a gearing unit forming a freewheel switchable in a direction of rotation which includes a first torque transmission sleeve/torque transmission element coupled in a rotationally and axially fixed manner in/to the torque introducing member/ratchet input component and a second torque transmission sleeve/torque transmission element coupled in a rotationally fixed and axially movable manner in/to the torque introducing member/ratchet input component, the first and second torque transmission sleeve/torque transmission elements comprising gearings acting in opposite directions and which can be meshed in response to a manually adjustable axial position of the second torque transmission sleeve, the tool fitting attachment further comprising an intermediate sleeve/selection component arranged to be axially movable as well as biased toward the gearings of the torque transmission sleeves/torque transmission elements, which intermediate sleeve/selection component is coupled to the guide shaft/ratchet output component via a torque.

3. The tool fitting attachment according to claim 2, wherein the guide shaft/ratchet output component in its function as the disconnect coupling includes an axially acting driver acting on the intermediate sleeve/selection component and displacing the intermediate sleeve/selection component at the first movement position of the guide shaft/ratchet output component relative to the gearings in a direction outside a meshing option so as to put the ratchet unit out of operation and moving the intermediate sleeve/selection component at the second movement position of the guide shaft relative to the two gearings in a direction within a meshing option so as to put the ratchet unit into operation.

4. The tool fitting attachment according to claim 3, wherein the guide shaft/ratchet output component includes a torque-transmitting engaging portion via which at the first movement position of the guide shaft/ratchet output component, torque engagement with the drive-side coupling can be produced while the ratchet unit is put out of operation.

5. The tool fitting attachment according to claim 1, further comprising a torque limiter.

6. The tool fitting attachment according to claim 5, wherein the torque limiter is arranged between the output-side coupling and the ratchet unit.

7. The tool fitting attachment according to claim 1, wherein the manually operated drive unit is connected to a ratchet unit or a pawl or is integrated with said ratchet unit or pawl.

8. The tool fitting attachment according to claim 7, wherein the manually operated drive unit is connected to said ratchet unit, the ratchet unit being in the form of a mechanical ratchet and can be changed between a clockwise rotation and an anti-clockwise rotation via a direction selection control unit.

9. The tool fitting attachment according to claim 8, wherein the direction selection control unit is integrated so that actuation is possible during electrical operation only.

10. The tool fitting attachment according to claim 7, further comprising a torque limiter.

11. The tool fitting attachment according to claim 10, wherein the manually operated drive unit is connected to said ratchet unit, and wherein the torque limiter is arranged between the output-side coupling and the ratchet unit.

12. The tool fitting attachment according to claim 7, wherein the manually operated drive unit is connected to a disconnect coupling so that upon actuation of the manually operated drive unit, a motor-driven torque transmission to the output-side coupling is rendered impossible.

13. The tool fitting attachment according to claim 12, wherein the disconnect coupling is connected to a manual-grip lever of the manually operated drive unit so that upon actuation of the manual-grip lever the disconnect coupling is actuated.

14. The tool fitting attachment according to claim 1, wherein the manually operated drive unit is connected to a manual-grip lever.

15. A surgical drill comprising:
an electric motor which is connected to the tool fitting attachment of claim 1 via the drive-side coupling of the tool fitting attachment for introducing a torque to the tool fitting attachment.

\* \* \* \* \*